US011911162B2

(12) United States Patent
Freycenon et al.

(10) Patent No.: US 11,911,162 B2
(45) Date of Patent: Feb. 27, 2024

(54) SYSTEM AND METHOD FOR DETERMINING A PULSE RATE BY PREDICTIVE FILTERING AND INTERCORRELATION OF SOUNDS SENSED IN A TRACHEA OF AN INDIVIDUAL

(71) Applicant: CONTROLE INSTRUMENTATION ET DIAGNOSTIC ELECTRONIQUES—CIDELEC, Sainte-Gemmes-sur-Loire (FR)

(72) Inventors: Nathalie Freycenon, Brissac-Loire-Aubance (FR); Roberto Longo, Angers (FR)

(73) Assignee: CONTROLE INSTRUMENTATION ET DIAGNOSTIC ELECTRONIQUES—CIDELEC, Sainte-Gemmes-sur-Loire (FR)

( * ) Notice: Subject to any disclaimer, the term of this patent is extended or adjusted under 35 U.S.C. 154(b) by 408 days.

(21) Appl. No.: 17/155,740

(22) Filed: Jan. 22, 2021

(65) Prior Publication Data
US 2021/0228135 A1     Jul. 29, 2021

(30) Foreign Application Priority Data
Jan. 23, 2020 (EP) .................................... 20153481

(51) Int. Cl.
A61B 5/00 (2006.01)
A61B 5/285 (2021.01)

(52) U.S. Cl.
CPC ............ *A61B 5/285* (2021.01); *A61B 5/4818* (2013.01); *A61B 5/725* (2013.01); *A61B 2562/0247* (2013.01)

(58) Field of Classification Search
None
See application file for complete search history.

(56) References Cited

U.S. PATENT DOCUMENTS 9,931,073 B2 * 4/2018 Moussavi ............ A61B 5/0826
10,441,181 B1 10/2019 Telefort et al.
(Continued)

FOREIGN PATENT DOCUMENTS

FR     2997600 A1    5/2014
WO     2005096931 A1 10/2005

OTHER PUBLICATIONS

English translation of Written Opinion dated Jul. 7, 2020 for corresponding European Application 20153481.5, filed Jan. 23, 2020.

(Continued)

*Primary Examiner* — Catherine M Voorhees
*Assistant Examiner* — Elizabeth K So
(74) *Attorney, Agent, or Firm* — David D. Brush; Westman, Champlin & Koehler, P.A.

(57) ABSTRACT

A method is proposed for determining a pulse rate through a sound-sensing means placed on an individual's trachea, the method comprising a preliminary step for recording sound signals for a lengthy duration, wherein it comprises subsequently the following steps: filtering digital signals representative of the sound signals by using an adaptive filter, applying a lowpass filter to the signals obtained in order to select the signals comprised in a specified passband, selecting a first temporal portion of filtered digital signals of a specified duration, intercorrelation with a temporal portion of filtered digital signals that follows the first temporal portion in time and is of a same duration, searching (4.6) for the intercorrelation, computing the time interval corresponding to this temporal position and computing the corresponding pulse rate throughout the recording duration, to obtain a temporal series of pulse rates S1.

9 Claims, 5 Drawing Sheets

(56) References Cited

U.S. PATENT DOCUMENTS

| | | |
|---|---|---|
| 2006/0287606 A1 | 12/2006 | Hong et al. |
| 2014/0180154 A1* | 6/2014 | Sierra ................. A61B 5/0205 |
| | | 600/529 |
| 2018/0014789 A1 | 1/2018 | Sato |

OTHER PUBLICATIONS

European Search Report and Written Opinion dated Jul. 7, 2020 for corresponding European Application 20153481.5, filed Jan. 23, 2020.

* cited by examiner

SYSTEM AND METHOD FOR DETERMINING A PULSE RATE BY PREDICTIVE FILTERING AND INTERCORRELATION OF SOUNDS SENSED IN A TRACHEA OF AN INDIVIDUAL

1. FIELD OF THE INVENTION

The present invention relates to a method for determining an individual's pulse rate by using sound signals provided by a microphone. The invention relates more particularly to the fact that the sound signals are above all intended for the detection of sleep apnea and that the method uses properties of predictive filtering and intercorrelation.

2. TECHNOLOGICAL BACKGROUND

Individuals can suffer from a medical condition known as sleep apnea syndrome in which respiration is stopped during sleep. These absences of respiratory cycles, which last more than ten seconds, impair the quality of sleep and cause a reduction of the oxygen level in the arterial blood. The reduction of oxygen gradually causes deterioration of the brain and heart functions, and the increase in micro-arousals prevents the brain from entering the phase of deep sleep. Individuals affected by this medical condition have a greater risk of cardiovascular events and daytime somnolence, which is responsible especially for road traffic accidents or accidents at work. There is therefore a need for medical instrumentation capable of detecting this type of pathology in patients in order to inform them of their condition and treat them. The analysis of sleeping disorders relies on the exploration of ventilation and of the stages of sleep. To detect this pathology, an instrument records the patient's respiratory behavior during sleep by using various sensors such as pulse oximeters, nasal probes, and thoracic and abdominal belts. A software program analyses the measurements in order to identify pathological events if any, such as apnea and hyperpnea. The pulse rate can be useful in tracking or diagnosing sleep apnea syndrome. Indeed, the pulse rate gets reduced in the sleeping state, thus giving an indication on the patient's sleep.

In sleep apnea, the pulse rate will get even further reduced, and then accelerate during the micro-arousals that generally follow the apnea episodes. Detecting such variations and correlating them with an absence of sound that reveals a stoppage of ventilation enables this diagnosis to be confirmed.

The number of sensors placed on the patient at night is a significant factor. The French patent application number FR1260312 filed on Oct. 30, 2012 by the present Applicant discloses a detector capable of determining the respiratory characteristics of a patient during sleep and detecting the presence of apnea if any. The detector comprises a microphone delivering signals representing the sound entering by the first aperture and a pressure sensor delivering signals representing a static pressure. Such a detector however cannot be used to provide high precision for computing pulse rates. Indeed, the sensed sound can be very noisy, especially because of snoring or because of the individual's movements when he is asleep.

3. GOALS OF THE INVENTION

There is therefore a real need for a method for analyzing the sounds sensed by a detector placed on a sleeping individual in order to determine his or her pulse rate and provide information on his or her ventilation. The acoustic signals of the respiration are then correlated with variations in pulse rate to either confirm or rule out the presence of sleep apnea and/or hyperpnea.

4. PRESENTATION OF THE INVENTION

One particular embodiment of the invention proposes a method for determining a pulse rate through the use of a sound-sensing means placed on an individual's trachea, the method comprising a preliminary step for recording sound signals for a lengthy duration. The method furthermore comprises the subsequent execution of the following steps:
  filtering digital signals representative of the sound signals by using an adaptive filter,
  applying a lowpass filter to the signals obtained in order to select the signals comprised in a specified passband,
  selecting a first temporal portion of filtered digital signals of a specified duration,
  intercorrelation with a temporal portion of filtered digital signals that follows the first temporal portion in time and is of a same duration,
  searching for the intercorrelation maximum for each portion of the temporal position,
  computing the time interval corresponding to this temporal position and computing the corresponding pulse rate,
  repeating the steps of selection, intercorrelation, searching for the maximum, and computing the pulse rate throughout the duration of the recording, to obtain a temporal series of pulse rates Sf.

Thus; the invention enables the measurement of a patient's pulse rate for a lengthy period of measurement, for example an entire night and, by correlating the acoustic signals of the respiration with the variations in pulse rate, the presence of sleep apnea and/or hyperpnea can be deduced therefrom.

According to a first embodiment, the steps of selection, intercorrelation and computation are applied successively to the digital signals by shifting the initial window, each time by a fraction of its duration. This then leads to several additional temporal series S2, S3, etc. of pulse rates, and the pulse rate chosen to build the final temporal series Sf at a given point in time is chosen from among the different temporal series. In this way, it is possible all the same to generate an intercorrelation even if the noises B1 and B2 are not present or are only partially present in the two windows.

According to another embodiment, the adaptive filter is a predictive filter.

According to another embodiment, the final temporal series Sf is built by choosing, for each element, the value in the temporal series for which the difference between the current value and the median value is the lowest.

According to another embodiment, the specified duration of the temporal portions of the filtered digital signals is appreciably one second.

According to another embodiment, the method comprises a step of comparison of each pulse rate with a mean value computed on the period and a step of replacement of the pulse rate value by the mean value if the pulse rate value diverges beyond a threshold of the mean value.

According to another embodiment, the detection and the correction of an abnormal value consists in building a temporal series of temporary pulse rate St by filtering the temporal series of final pulse rate Sf with a lowpass filter, and replacing the values of the temporal series Sf by those of St when the divergence between the two values is excessively great.

According to another embodiment, if the mean pulse rate Fm is very distant from the inverse of the duration of the temporal portion chosen during the step for selecting a first temporal portion, then all the operations are restarted in adapting the duration of temporal portion to the mean frequency Fm.

According to another embodiment, the sound-sensing means is a microphone or a pressure sensor.

5. DESCRIPTION OF THE FIGURES

Other features and advantages of the invention shall appear from the following description, given by way of an indicative and non-exhaustive example and from the appended drawings, of which.

6. DETAILED DESCRIPTION OF ONE EMBODIMENT

6.1 General Principle

The general principle of the invention relies on a method for determining a pulse rate through a sound-sensing means placed on an individual's trachea. This method comprises a preliminary step for recording sound signals over a lengthy duration, for example one night. A processing operation is then applied to the recorded signals by the following steps: filtering the digital signals representative of the sound signals by using a predictive filter, applying a lowpass filter to the signals obtained in order to select signals comprised in a specified bandwidth, selecting a first temporal portion of filtered digital signals of a specified duration comprising two cardiac signals belonging to a same first cardiac cycle, determining by intercorrelation with a second temporal portion of filtered digital signals of a same specified duration, and comprising also the two same cardiac signals belonging to a second cardiac cycle, computing the duration between the instants separating the same signals of the two temporal portions, and determining the pulse rate by taking the inverse of this duration.

6.2 Description of One Embodiment

Figure 1:
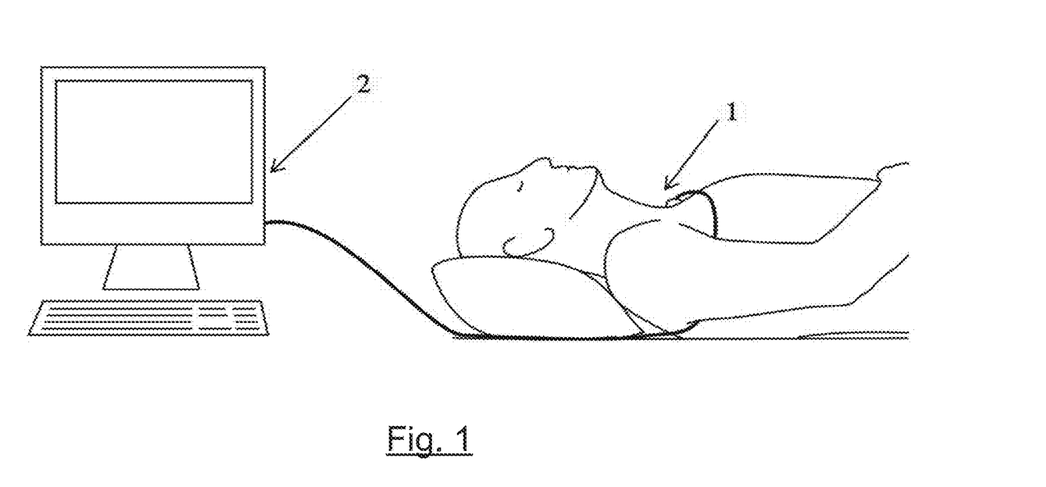
FIG. 1 presents an individual in a sleeping position with a sound detector connected to a processing unit.

FIG. 1 presents an individual in a sleeping position with a sound detector connected to a processing unit. The sound detector 1 is placed at the base of the individual's neck above his trachea or windpipe. It is if necessary held by a medical adhesive. According to a preferred embodiment, the detector 1 has an electrical cable connected to a processing unit 2 that analyses the sound signals emitted by the individual and determines his respiratory characteristics: inhalation, exhalation, apnea, hyperpnea, glottal movements, etc. According to one alternative embodiment, the sound detector communicates by a short-range wireless link (of the Bluetooth type, for example).

From a mechanical viewpoint, the individual's epidermis is similar to an elastic wall. The airflow moving in the throat and the trachea or windpipe generates sounds that get propagated through the individual's various tissues and are perfectly audible through the epidermis and the skin surface.

Figure 2:
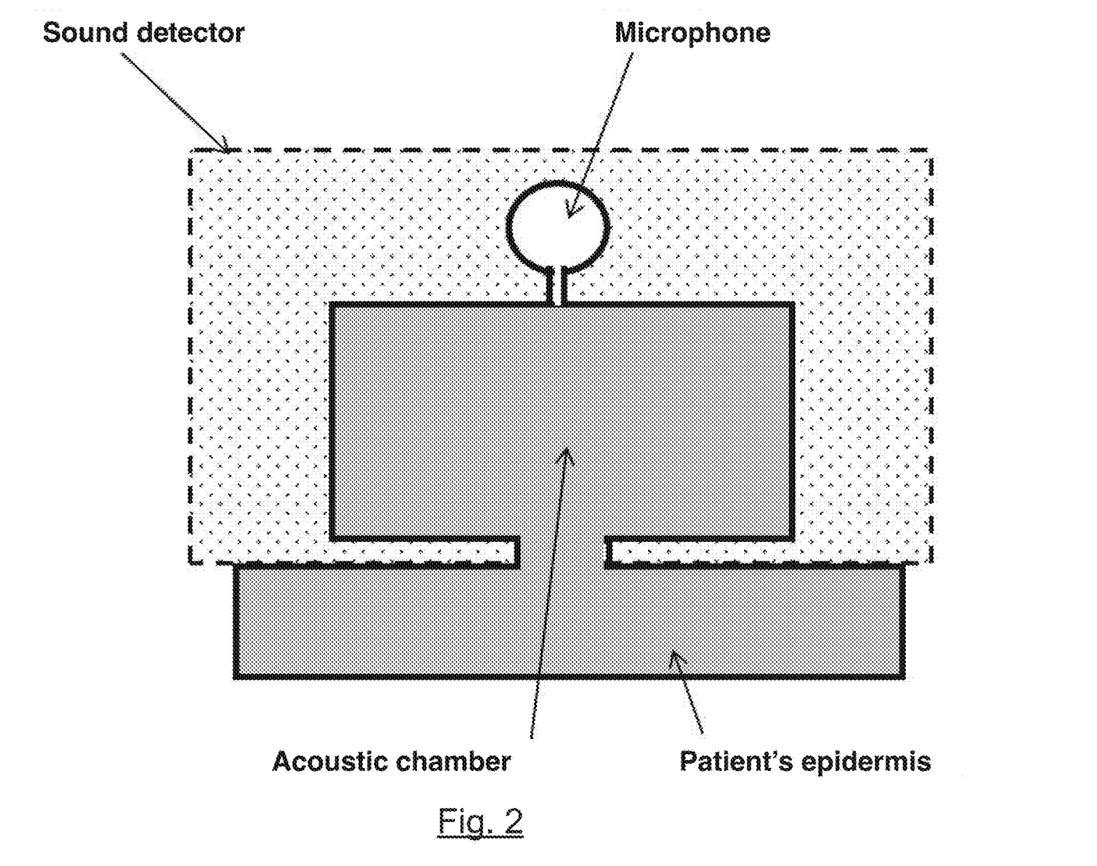
FIG. 2 is a drawing of a sound detector according to one preferred example of an embodiment.

FIG. 2 presents a drawing of a sound detector according to a preferred embodiment. The lower part of the detector is constituted by an acoustic chamber opening into a vent that gets placed on the patient's epidermis. Since the edge of the vent is in contact with the epidermis, the acoustic chamber constitutes a closed cavity. Hence, the variations in pressure in the acoustic chamber depend on the sounds and on the pressure prompted by the respiration and the respiratory movements. A microphone is placed in acoustic communication with the chamber to detect the sound waves. To measure a wide range of acoustic frequency, the microphone possesses a fairly large bandwidth extending from 10 Hz to 10 kHz. The microphone detects the sounds inside the acoustic chamber, which are transmitted by the patient's epidermis, and converts them into electrical signals that are sent towards the processing unit. The microphone emits electrical signals representative of the sensed sound towards the analog-digital converter (ADC) which is a circuit intended to convert analog signals into digital signals. The ADC converter samples the analog signals at a frequency that is high enough to sense the sound variations, even the fine variations, and to deduce therefrom especially the phases of the cardiac cycle as a function of the noises emitted by the heart.

The heart is a muscle the function of which is to pump blood about 100,000 times per day. The heart is composed of four parts called cavities. The upper two cavities are called atria and the lower two cavities are called ventricles. The four cavities communicate with each other by means of valves that open and shut as a function of the variations in pressure of the different heart cavities. Each atrium is separated from the ventricle by a valve: to the right, there is the tricuspid valve and to the left the mitral valve. The aortic valve separates the left ventricle from the aorta and the pulmonary valve separates the right ventricle from the pulmonary aorta. These valves, like non-return check valves, dictate the sense or direction of circulation of the blood in the heart. The left side of the heart sends oxygen-rich blood, coming from the pulmonary vein towards the systemic circulation, to transport it towards all the tissues of the organism apart from the pulmonary alveoli. The right side of the heart pumps oxygen-depleted blood coming from the organs in order to transport it towards the pulmonary alveoli where it gets rid of carbon gas and is recharged with oxygen. The heart works in cycles. The cardiac cycle consists of a succession of contractions and relaxations of the muscle and of opening and shutting of the valves. A cardiac cycle can be divided into two main periods: a phase during which the ventricle contracts (systole) with ejection of blood that alternates with a phase of relaxation and filling of the ventricle (diastole).

Since the cardiac activity is mechanical, it produces sound waves, the recording of which, called a phonocardiogram, is generally performed on the front side of the thorax using an electronic stethoscope. These mechanical noises are produced by the flow of blood through the different cavities, and the shutting and opening of the valves. During a cardiac cycle, four noises are sent out by the heart and are named B1, B2, B3 and B4, it being known that the noises B1 and B2 have amplitudes higher than those of B3 and B4. This is why the present invention uses the acoustic trace of the noises B1 and B2 to determine the pulse rate.

Figure 3:
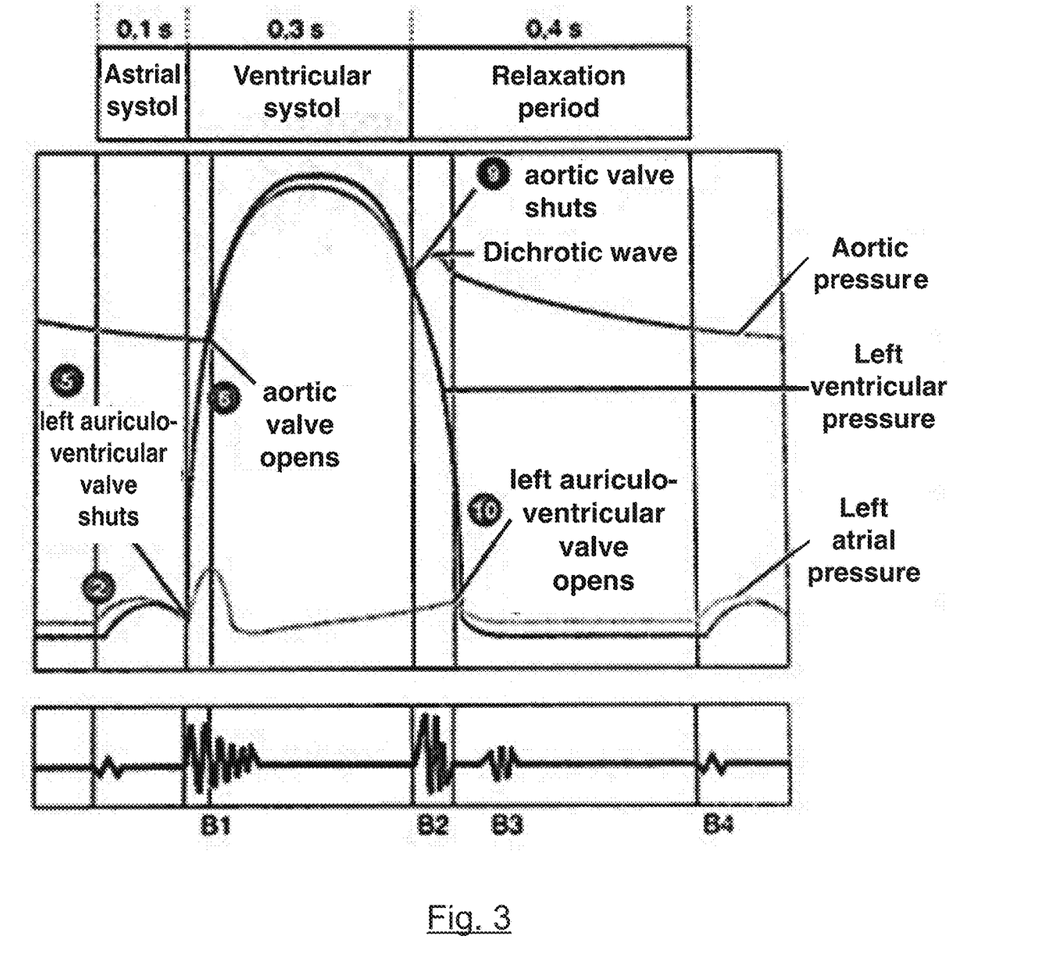
FIG. 3 is a drawing illustrating the succession of noises B1 to B4 emitted by the heart during a cardiac cycle.

FIG. 3 illustrates the succession of noises B1 to B4 emitted by the heart during the cardiac cycle. FIG. 3 includes an upper strip or band presenting the three main phases: atrial systole, ventricular systole and period of relaxation, a central part showing the variations in pressure at the level of the aorta, the left ventricle and the left atrium and a lower strip representing a phonocardiogram with a location in time of the noises B1 to B4.

Each of the noises has a particular and recognizable acoustic trace. The characterization of these traits is described in the thesis by Ali Moukadem, "Segmentation and classification of non-stationary signals: application to the processing of heart sounds and to aid in diagnosis" defended on Dec. 16, 2011 at Mulhouse, France. We may recall the essential characteristics of these noises. The noise B1 is a resonant noise, more intense and slightly longer than the second noise B2. The noise B1 has two sound components: a valvular noise and a muscular noise. The first component is related to the closing of the atrial-ventricular valves (tricuspid and mitral valves) and the second to the sudden contraction of the heart muscle, at the start of the ventricular systole. The noise B2 corresponds to the shutting of the aortic and pulmonary valves at the start of the ventricular diastole. The noise B3 has low amplitude and is audible mainly in children (aged up to 16 years). The noise B3 corresponds to the turbulence of the blood during the fast ventricular filling phase. The noise B4 is emitted during the atrial systole phase which consists in the filling of the ventricle by the contraction of the atrium. For a healthy adult, the noises B3 and B4 are almost inaudible, and their appearance in a recording is therefore a pathological sign. Other abnormal noises such as heart murmur, diastolic noises or systolic noises are also pathological signs.

The upper band of FIG. 3 shows that, for a cardiac cycle of 0.8 seconds corresponding to a heart rate of 75 bpm (beats per minute), the different phases last for the following amount of time:
  the atrial systole phase (between B4 and B1) lasts 0.1 seconds,
  the ventricular systole phase (between B1 and B2) lasts 0.3 seconds,
  the period of relaxation (between B2 and B4) lasts 0.4 seconds.

The invention can be used especially to detect the presence of groups of noises B1 and B2 and measure the durations between these groups in order to determine characteristics of heart functioning and especially the pulse rate. This determination can be done by a software module embedded in a computer such as a processing unit 2 that receives the digital signals emitted by the ADC converter.

Figure 4:
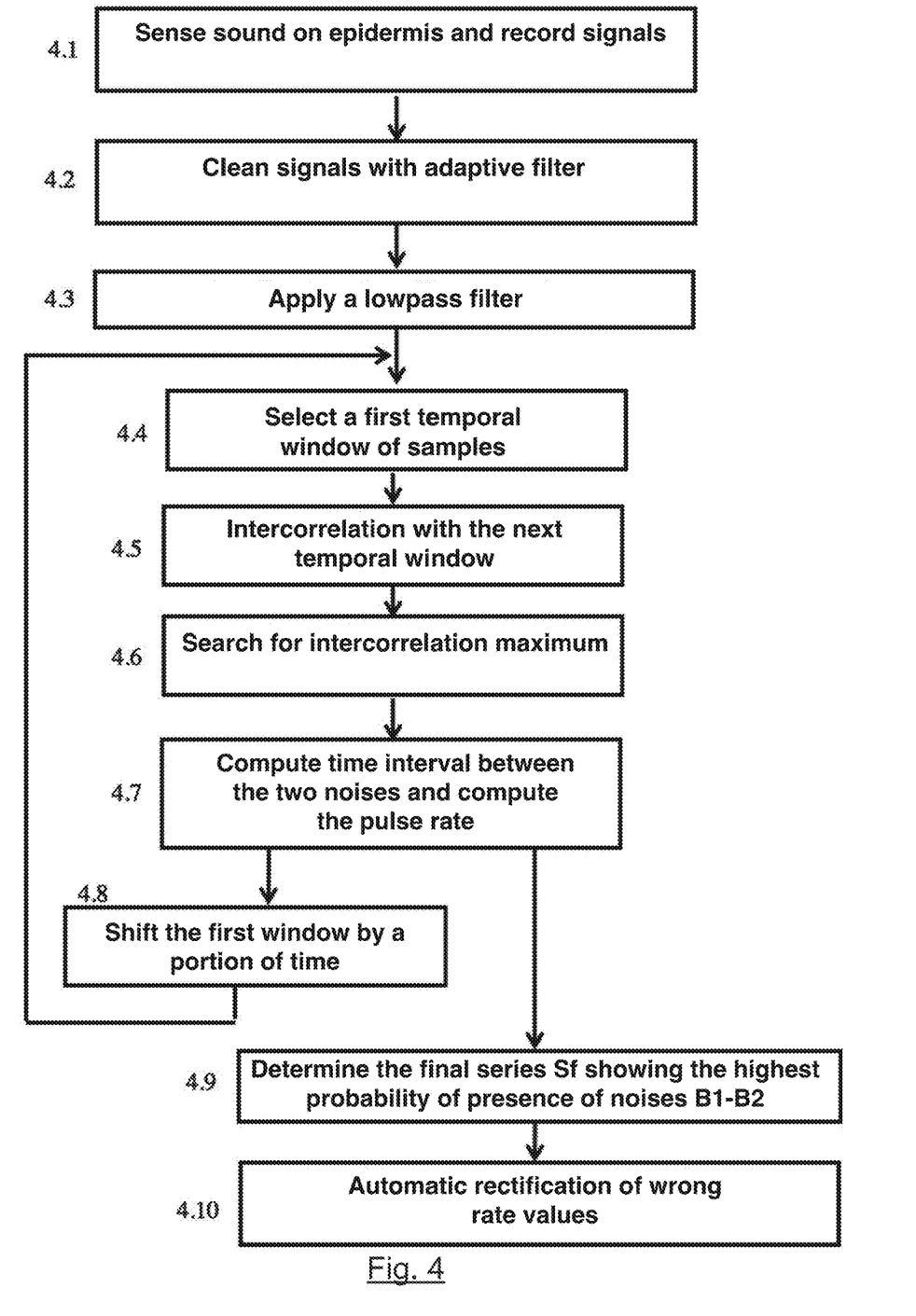
FIG. 4 presents a flowchart of the main steps of the method for determining a pulse rate according to a preferred example of an embodiment.

FIG. 4 is a flowchart of the main steps of the determination of a pulse rate. A patient is stretched out on a bed and a health practitioner installs a sound detector at the level of his trachea. In the case of an apnea-related analysis, the signals are collected at night when the patient is asleep. At the step 4.1, the acoustic signal is sensed by the microphone and then sent in the form of electrical signals to an ADC converter which produces digital signals. These digital signals are recorded in a computer memory to constitute "raw data". These data can be noisy, especially because of the patient's snoring or because of the movements of the individual during his sleep. The raw data are first of all cleaned by using an adaptive filter so as to reduce the scale of the noise (step 4.2). This filter is advantageously of the predictive type.

Figure 6:
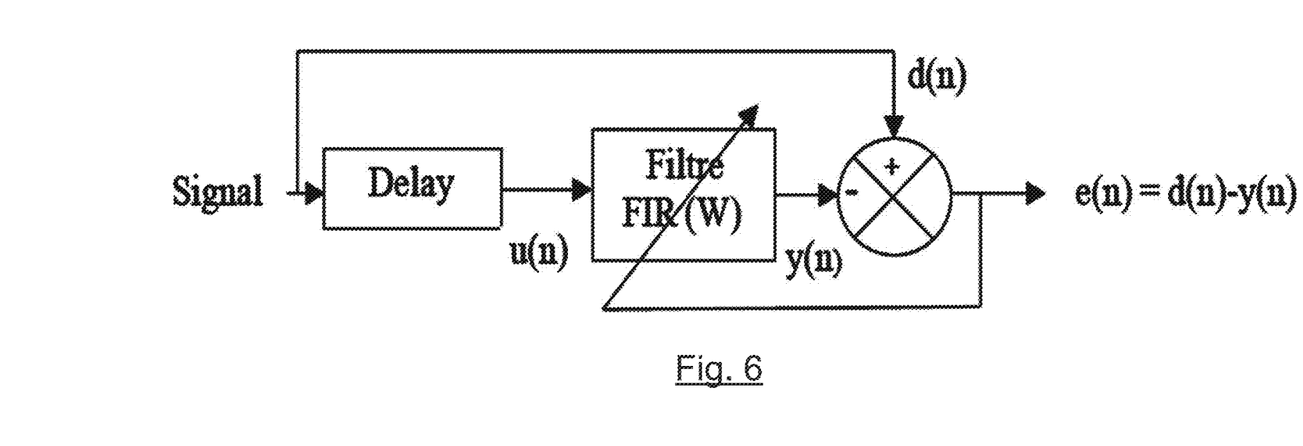
FIG. 6 represents a drawing illustrating the principle of a predictive filter that can be used for the present invention.

The predictive filter present in FIG. 6. is constituted by the following elements:
An FIR filter W with M coefficients, a time lag $\Delta$.
The signals are real and discrete, and at the instant n, the following signals are noted:
  $d(n)$: the value of the input signal (reference signal),
  $u(n)$: the input signal delayed $u(n)=d(n-\Delta)$,
  $y(n)$: the output of the filter W,
  $e(n)$: the estimated error: $e(n)=d(n)-y(n)$.
  $y(n)$ is the output of the predictive filter.

The M coefficients of the filter W are defined by an iterative process following the Least-Mean-Square (LMS) algorithm proposed by Widrow and Hoff (references: Widrow, B., and Hoff, M. E., 1960, Adaptive switching circuits: IRE WESCON Cony. Rec., pt. 4, p 96-104. Widrow, B., and Stearns, S., 1985, Adaptive Signal Processing: Prentice-Hall, New York).

The M coefficients of the filter at the instant $n+1$ are then determined by the relationship:

$$W(n+1) = W(n) + 2\mu e(n)U(n),$$

with
$$W = [w_0 w_1 \ldots w_{M-1}]$$
and
$$U(n) = [u(n)u(n-1)\ldots u(n-M+1)]$$

An alternative way of computing the optimal coefficients of the filter W is to resolve the classic Wiener problem:

$$W_{opt}=R^{-1}P.$$

where R represents the self-correlation matrix of the input $U(n)$ and P the intercorrelation matrix between the inputs of the filter $U(n)$ and the reference signal $d(n)$.

Figure 5:
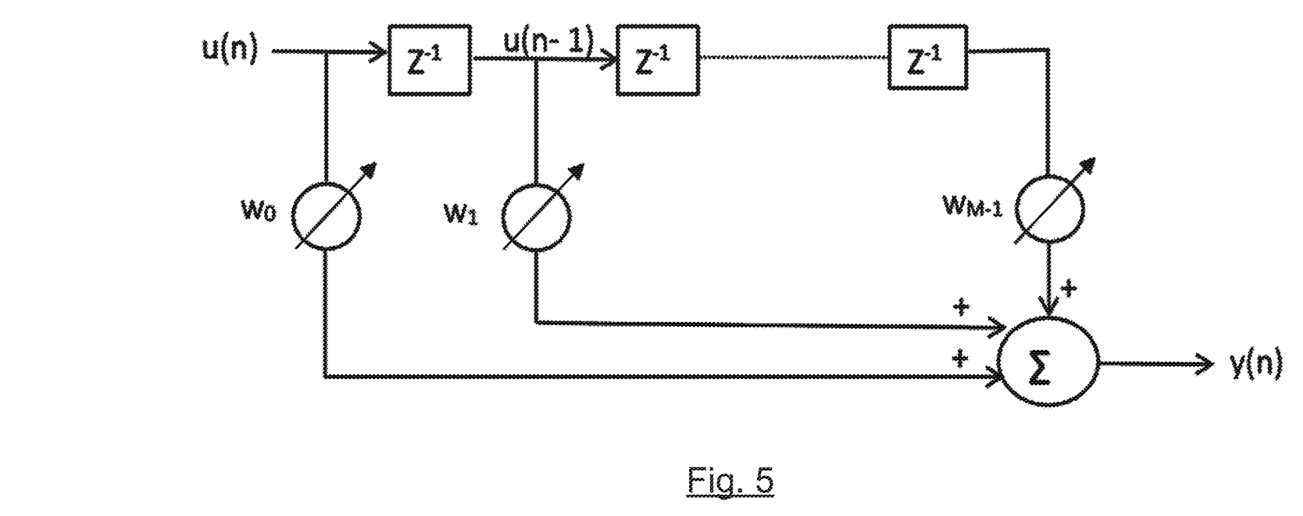
FIG. 5 represents the structure of a finite response (FIR) linear filter that can be used for the present invention.

The Weiner solution is described in detail here below.
The structure of the finite impulse response (FIR) linear filter is shown in FIG. 5. The goal is to compute the coefficients $\omega_k$ of the linear filter by having recourse to the mean quadratic error.

This error must be minimal in order to obtain a better filter so that the output of the filter approaches the desired signal to the best possible extent.

The output of the filter (FIR) $y(n)$ is then written as:

$$y(n) = \sum_{k=0}^{M-1} w_k u(u-k) = W^T U(n),$$

with (the symbol T representing the transpose of the vector)

$$W^T=[w_0,w_1,\ldots,w_{M-1}]$$

$$U(n)=[u(n)u(n-1)\ldots u(n-M+1)]^T$$

The error is then written as:

$$e(n)=d(n)-y(n)=d(n)-W^T U(n),$$

The quadratic error therefore has the following expression:

$$e^2(n)=(d(n)-W^T U(n))^2=d^2(n)+W^T U(n)U^T(n)W-2d(n)W^T U(n)$$

Assuming that the process is a second-order stochastic and stationary process, the mean quadratic error is computed as follows:

$$E[e^2(n)] = \sigma_d^2 - 2P^T W(n) + W^T(n) R W(n)$$

with $$P = P_{dU} = E[d(n)U(n)]$$

$$R = R_{uu} = E[U(n)U^T(n)]$$

R herein represents the self-correlation matrix of the input U(n) and P the intercorrelation matrix between the inputs of the filter and the desired output. The mean quadratic error can thus be minimized by computing the coefficients $\omega_k$ of the optimal filter. To this end, the Weiner solution teaches:

$$\frac{\partial E[e^2(n)]}{\partial w_k(n)} = 0$$

The above equation can be expressed equivalently:

$$2RW(n) - 2P(n) = 0$$

With $W_{opt}$ denoting the optimal solution and the matrix R being considered to be reversible, we can conclude by the following expression:

$$W_{opt} = R^{-1} P.$$

At the step 4.3, the signals cleaned by the predictive filtering, for example by an LMS-type predictive algorithm, pass through a lowpass filter according to a technique known per se. This lowpass filter is for example of the Butterworth type, with a 35 Hz cut-off frequency. At output of the lowpass filter, the filtered digital signals are recorded and ready to be processed.

The measurements are made on a patient at rest and preferably asleep. In these conditions, this patient's pulse rate ranges from 40 bpm to 120 bpm. The ADC converter samples the sound signal at the frequency of 4000 Hz (Fs). Thus, one cardiac cycle is covered by a recording of 2000 to 6000 measurement samples. The acoustic trace of a cardiac cycle according to the present invention is demarcated in time between the noises B1-B2 of one cardiac cycle and the noise B1-B2 of the next cardiac cycle. To evaluate this time, the invention provides for implementing the intercorrelation by a sliding window that is an efficient method for determining the time difference between repetitive patterns in an environment liable to be noisy.

The step 4.4 consists in extracting a first window of a specified number of data samples obtained by filtering. This first window then possesses a specified duration, typically one second. The content of this first window is correlated at the step 4.5 with the following window which possesses the same specified number of points, and therefore has the same duration. If the noises B1 and B2 are present in the two successive windows, then the temporal position of the intercorrelation maximum provides information on the time between a group of two noises B1 and B2 of the first window and the group of two noises B1 and B2 of the second window. The temporal position of the intercorrelation maximum is determined (step 4.6). At the step 4.7, the method computes the time interval corresponding to this temporal position.

Then, the pulse rate is then computed by taking the inverse of this duration. Multiplied by 60, this value is expressed by beats per minute (bpm). This operation is done throughout the duration of the recording with all the successive temporal windows. We thus obtain a temporal series FreqCard (BMP). When the noises B1 and B2 are not present or are only partially present in the two windows, the intercorrelation cannot generate a correct piece of information. To overcome this difficulty, the above-described operations are repeated several times in shifting the first window by a fraction of its duration (step 4.8). In this way, it is possible to increase the probability of detecting an interconnection between two contiguous windows having successive noises B1 and B2. At the end of these operations, there are several temporal series S1, S2, S3, etc., each of which have true values and false values. The result of this mode of operation is that these temporal series are sampled at the frequency 1/DT.

At the step 4.9, the different series are scanned through simultaneously to choose, from among them, the value to be preserved for the given point in time and to generate a single temporal series Sf of pulse rate.

In a first stage, excessively small or excessively great values can be eliminated. Then, different means implementing probability techniques can be used to choose, at each point in time, that temporal series in which S takes the value of the pulse rate.

According to a preferred embodiment, for each temporal series obtained at the end of the steps 4.4 to 4.7 and in taking account of the shift (step 4.8), the module computes the median value (for example O=17) around the current value as well as the divergence E between the current value and the median value. The module then chooses the pulse rate of the series for which the divergence E is the lowest.

The single temporal series Sf thus obtained can again be vitiated by errors. A final step 4.10 can then be implemented to eliminate the errors. Different techniques can be used.

According to a preferred embodiment, the module computes the absolute value of the difference between the preceding value and the next value. If this number is smaller than a certain threshold (for example 3 bpm), then the module considers that the pulse rate is locally stable. The current value should not be far too distant from the mean value. If the current value is far too distant (for example 10 bpm), then the module replaces it with the mean value.

It is also possible to filter the temporal series with a lowpass filter, for example a fourth-order lowpass filter, with a cut-off frequency at ⅓₀ of the sampling frequency of the temporal series S, i.e.: (1/DT)/30. Then, the values of the initial series that would be far too divergent from the filtered value are replaced by the filtered value.

Figure 7:
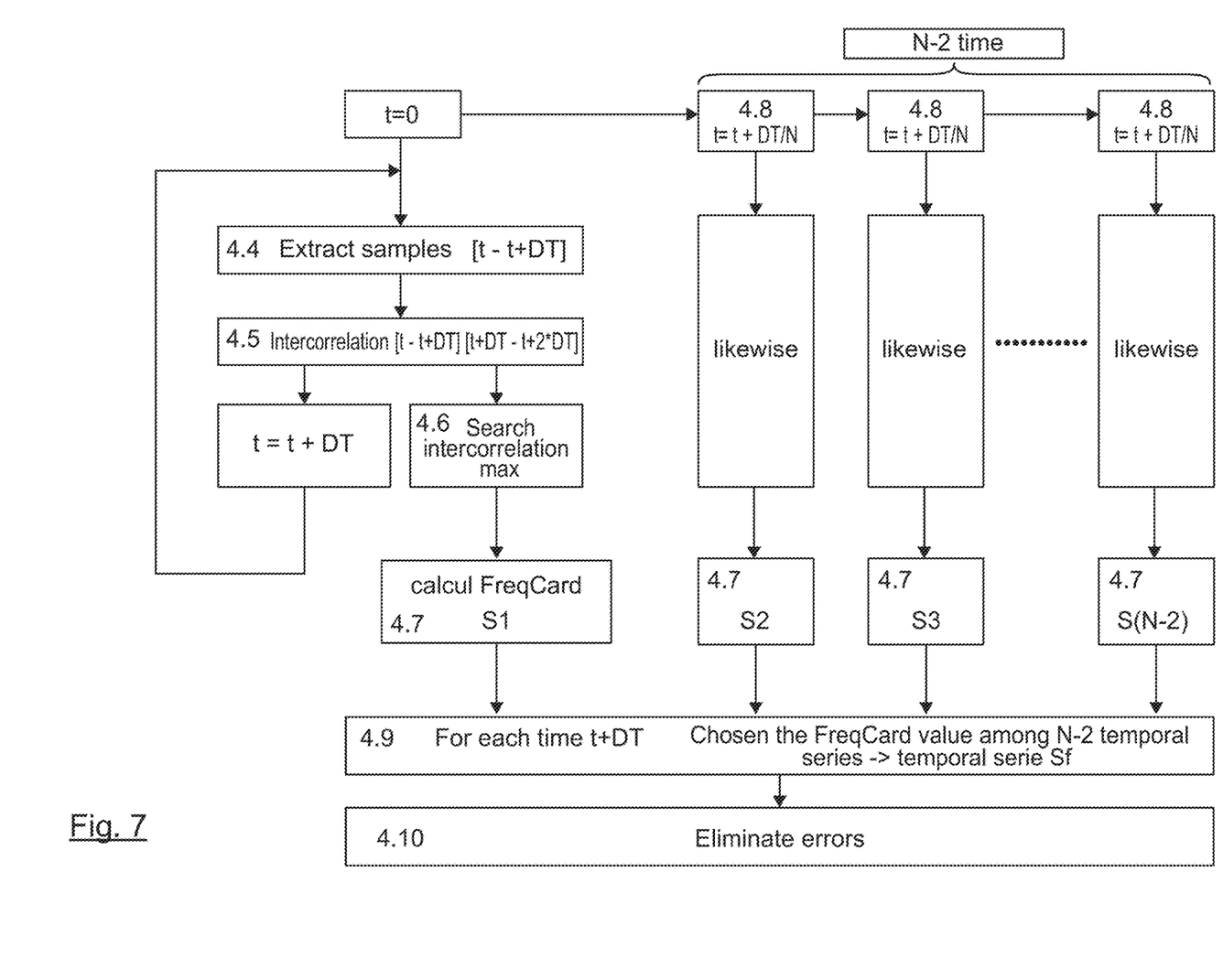
FIG. 7 is a flowchart of a part of the steps according to one particular example of an embodiment.

FIG. 7 presents a flowchart of a part of the steps according to one particular embodiment. The steps of FIG. 4 are reproduced therein by specifying the execution times and the succession of operations. This figure shows especially the steps forming the loop leading to the generation of each temporal series S1, S2, S3, etc. The search for the intercorrelation maximum (step 4.6) can be used to determine the time interval between the temporal positions of the maximum values of intercorrelation of the first window and of the next window and to deduce the pulse rate therefrom by computing the inverse of this duration (step 4.7). The processing of the data of each loop is done by shifting the first window by a duration DT (step 4.8). For each instant t+DT, the value of the pulse rate to be kept is chosen from among the temporal series thus generated to build the final temporal series Sf (step 4.9). The optional final step 4.10 consists in rectifying errors if any by eliminating erroneous frequencies.

It should be obvious to those skilled in the art that the present invention enables embodiments in many other specific forms without departing from the field of application of the invention as claimed. The present embodiments and variants must therefore be considered by way of illustration but can be modified in the field defined by the scope of the appended claims.

The invention claimed is:

1. A method comprising:
    determining a pulse rate through use of a sound detector placed on an individual's trachea, the determining comprising the following acts:
    recording sound signals for a predefined duration;
    filtering digital signals representative of the sound signals by using a finite impulse response adaptive filter,
    applying a lowpass filter to the filtered digital signals in order to select signals comprised in a specified passband,
    selecting a first temporal portion of filtered digital signals of a specified duration,
    intercorrelating with a temporal portion of filtered digital signals that follows the first temporal portion in time and is of a same duration,
    searching for, for each portion, a temporal position of the intercorrelation maximum,
    computing a time interval corresponding to this temporal position and computing the pulse rate corresponding to this temporal position,
    repeating the acts of selecting, intercorrelating, searching, and computing the pulse rate throughout the predefined duration of the recording, to obtain a temporal series of pulse rates.

2. The method according to claim 1, wherein:
    the acts of selecting, intercorrelating, and computing the pulse rate are applied successively to the digital signals in shifting an initial window each time by a fraction of its duration, thus leading to several additional temporal series of pulse rates,
    the determining further comprising choosing a pulse rate to build a final temporal series at a given point in time from among the different temporal series.

3. The method according to claim 2, wherein the final temporal series is built by choosing, for each temporal series, a value in the temporal series for which the difference between the current value and the median value is the lowest.

4. The method according to claim 2, wherein method comprises comparing each pulse rate with a mean value computed on the predefined duration and replacing the pulse rate by the mean value if the pulse rate diverges beyond a threshold of the mean value, and wherein the replacing comprises building a temporal series of temporary pulse rates by filtering the final temporal series of pulse rates with a lowpass filter, and replacing values of the temporal series by those of the temporal series of temporary pulse rates when the two values differ by at least a predefined value.

5. The method according to claim 1, wherein the finite impulse response adaptive filter is a predictive filter.

6. The method according to claim 1, wherein the specified duration of the temporal portions of the filtered digital signals is appreciably one second.

7. The method according claim 1, wherein method comprises comparing each pulse rate with a mean value computed on the predefined duration and replacing the pulse rate by the mean value if the pulse rate diverges beyond a threshold of the mean value.

8. The method according to claim 7, wherein if the mean value differs by at least a predetermined value from an inverse of the specified duration of the first temporal portion chosen during the act of selecting, then all operations are restarted in adapting the specified duration of the first temporal portion to a mean frequency.

9. The method according to claim 1, wherein said sound detector is a microphone or a pressure sensor.

* * * * *